United States Patent
Meade et al.

(10) Patent No.: US 10,656,229 B2
(45) Date of Patent: May 19, 2020

(54) MAGNETIC BARCODE IMAGING

(71) Applicant: NORTHWESTERN UNIVERSITY, Evanston, IL (US)

(72) Inventors: Thomas J. Meade, Wilmette, IL (US); Hsiang-Hua Hung, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 303 days.

(21) Appl. No.: 15/479,821

(22) Filed: Apr. 5, 2017

(65) Prior Publication Data

US 2017/0293009 A1    Oct. 12, 2017

Related U.S. Application Data

(60) Provisional application No. 62/318,991, filed on Apr. 6, 2016.

(51) Int. Cl.
| | |
|---|---|
| *G01R 33/56* | (2006.01) |
| *A61B 5/055* | (2006.01) |
| *A61B 6/03* | (2006.01) |
| *A61B 5/00* | (2006.01) |
| *G01R 33/48* | (2006.01) |
| *G01R 33/50* | (2006.01) |
| *G01R 33/561* | (2006.01) |

(52) U.S. Cl.
CPC ........ *G01R 33/5601* (2013.01); *A61B 5/0035* (2013.01); *A61B 5/055* (2013.01); *A61B 5/7267* (2013.01); *A61B 6/037* (2013.01); *G01R 33/481* (2013.01); *G01R 33/50* (2013.01); *G01R 33/5616* (2013.01); *G01R 33/5617* (2013.01)

(58) Field of Classification Search
USPC .......................... 324/300–322; 600/407–435; 382/128–131
See application file for complete search history.

(56) References Cited

U.S. PATENT DOCUMENTS

| 8,781,197 B2* | 7/2014 | Wang ..................... G01R 33/54 382/131 |
|---|---|---|
| 9,370,316 B2 | 6/2016 | Ewing et al. |
| 2001/0021794 A1 | 9/2001 | Muraki et al. |
| 2011/0044524 A1* | 2/2011 | Wang ..................... G01R 33/54 382/131 |
| 2017/0293009 A1* | 10/2017 | Meade ............... G01R 33/5601 |

OTHER PUBLICATIONS

Alford et al., "Delta relaxation enhanced MR: improving activation-specificity of molecular probes through R1 dispersion imaging." Magn Reson Med. Apr. 2009;61(4):796-802.

Brown et al., "Neuroradiologic MR applications with multiparametric color composite display." Magn Reson Imaging. 1996;14(1):59-72.

(Continued)

*Primary Examiner* — Daniel R Miller
(74) *Attorney, Agent, or Firm* — Casimir Jones, S.C.; Tanya Arenson (57) ABSTRACT

Provided herein is technology relating to magnetic resonance imaging contrast agents and particularly, but not exclusively, to methods and systems for visualizing one or more magnetic resonance imaging contrast agent.

20 Claims, 4 Drawing Sheets

(56) References Cited

OTHER PUBLICATIONS

Clarke et a., "Quantitative assessment of carotid plaque composition using multicontrast MRI and registered histology." Magn Reson Med. Dec. 2003;50(6):1199-208.
Deoni et al., "High-resolution T1 and T2 mapping of the brain in a clinically acceptable time with DESPOT1 and DESPOT2." Magn Reson Med. Jan 2005;53(1):237-41.
Derochefort et al., "Quantitative susceptibility map reconstruction from MR phase data using bayesian regularization: validation and application to brain imaging." Magn Reson Med. Jan. 2010;63(1):194-206.
Frullano et al., "Bimodal MR-PET agent for Quantitative pH imaging." Angew Chem Int Ed Engl. Mar. 22, 2010;49(13):2382-4.
Frullano et al., "Multimodal MRI contrast agents." J Biol Inorg Chem. Sep. 2007;12(7):939-49.
Gao et al., "In vivo cancer targeting and imaging with semiconductor quantum dots." Nat Biotechnol. Aug. 2004; 22(8):969-76.
Harrison et al., "A multimeric MR-optical contrast agent for multimodal imaging." Chem Commun (Camb). Oct. 9, 2014;50(78):11469-71.
Khemtong et al., "In vivo off-resonance saturation magnetic resonance imaging of alphavbeta3-targeted superparamagnetic nanoparticles." Cancer Res. Feb. 15, 2009;69(4):1651-8.
Lee et al., "Artificially engineered magnetic nanoparticles for ultra-sensitive molecular imaging." Nat Med. Jan. 2007;13(1):95-9.
Liaw et al., ""Classification and Regression byrandomForest"" R News, vol. 2/3, Dec. 2002, p. 18-22.
Liu et al., "Morphology enabled dipole inversion for quantitative susceptibility mapping using structural consistency between the magnitude image and the susceptibility map." Neuroimage. Feb. 1, 2012;59(3):2560-8.
Liu et al., "Nonlinear formulation of the magnetic field to source relationship for robust quantitative susceptibility mapping." Magn Reson Med. Feb. 2013;69(2):467-76.
Liu et al., "Ultrashort T2* relaxometry for quantitation of highly concentrated superparamagnetic iron oxide (SPIO) nanoparticle labeled cells." Magn Reson Med. Apr. 2009;61(4):761-6.
Liu et al., "Unambiguous identification of superparamagnetic iron oxide particles through quantitative susceptibility mapping of the nonlinear response to magnetic fields." Magn Reson Imaging. Nov. 2010;28(9):1383-9.
Lustig et al., "Sparse MRI: The application of compressed sensing for rapid MR imaging." Magn Reson Med. Dec. 2007;58(6):1182-95.
Major et al., "The synthesis and in vitro testing of a zinc-activated MRI contrast agent." Proc Natl Acad Sci U S A. Aug. 28, 2007;104(35):13881-6.
Matosziuk et al., "Structural optimization of Zn(II)-activated magnetic resonance imaging probes." Inorg Chem. Nov. 4, 2013;52(21):12250-61.
Muraki et al., "An attempt for coloring multichannel MR imaging data" IEEE Transactions on Visualization and Computer Graphics, vol. 7, No. 3, 2001 p. 265-74.
Pruessmann et al., "SENSE: sensitivity encoding for fast MRI." Magn Reson Med. Nov. 1999;42(5):952-62.
Sherry et al., "Chemical exchange saturation transfer contrast agents for magnetic resonance imaging." Annu Rev Biomed Eng. 2008;10:391-411.
Shin et al., "$T_1$ and $T_2$ dual-mode MRI contrast agent for enhancing accuracy by engineered nanomaterials." ACS Nano. Apr. 22, 2014;8(4):3393-401.
Suykens et al., "Least Squares Support Vector Machine Classifiers" Neural Processing Letters 9: 293-300, 1999.
Warren et al., "MR imaging contrast enhancement based on intermolecular zero quantum coherences." Science. Jul. 10, 1998;281(5374):247-51.
Wheaton et al., "In vivo quantification of T1rho using a multislice spin-lock pulse sequence." Magn Reson Med. Dec. 2004;52(6):1453-8.
Wu et al., "Top 10 algorithms in data mining" Knowl Inf Syst (2008) 14:1-37.
Zavaleta et al., "Multiplexed imaging of surface enhanced Raman scattering nanotags in living mice using noninvasive Raman spectroscopy." Proc Natl Acad Sci U S A. Aug. 11, 2009;106(32):13511-6.
Hung et al., "High dynamic range processing for magnetic resonance imaging." PLoS One. Nov. 8, 2013;8(11):e77883.

* cited by examiner

MAGNETIC BARCODE IMAGING

CROSS REFERENCE TO RELATED APPLICATIONS

The present invention claims the priority benefit of U.S. Provisional Patent Application 62/318,991, filed Apr. 6, 2016, which is incorporated by reference in its entirety.

STATEMENT REGARDING FEDERALLY SPONSORED RESEARCH OR DEVELOPMENT

This invention was made with government support under R01EB005866, R01EB014806, and U54CA151880 awarded by the National Institutes of Health. The government has certain rights in the invention.

FIELD OF INVENTION

Provided herein is technology relating to magnetic resonance imaging contrast agents and particularly, but not exclusively, to methods and systems for visualizing one or more magnetic resonance imaging contrast agent.

BACKGROUND

Magnetic Resonance Imaging (MRI) is an imaging technique used in medicine. In this technique, images are obtained by applying a strong magnetic field, a magnetic-field gradient, and frequency-matched radio frequency (RF) pulses to a subject or sample. During the imaging process, atomic nuclei in the subject or sample, which have a magnetic moment and which are mostly protons, become excited by the RF radiation. When the RF pulse is stopped, relaxation of the excited nuclei causes emission of an RF signal that is detected. This signal is referred to as the free-induction decay (FID) response signal. As a result of applied magnetic-field gradients, the frequencies in this RF signal contain spatial information that are used to construct a gray scale image.

Since protons are the most abundant and sensitive nuclei in biological tissues, a majority of medical applications of MRI utilize images of protons. These MRI images primarily reflect the distribution of water in the subject (e.g., a human body) or sample, since the protons in biological tissue are present mainly as water. MRI images have an appearance which is similar to X-ray computerized tomography (CT) scan images, but MRI images are based on differences in water content and differences in relaxation rates of water in various body tissues rather than on differences in the absorption of X-rays between various tissues of the body.

More specifically, in MR imaging the subject or sample is placed in a static magnetic field (a biasing field) and then excitation signals are applied to induce a response. Time varying magnetic fields (gradient fields) permit localized points in the tissue volume to be addressed. Sequences of radio frequency pulses excite nuclei that respond at specific RF pulse frequencies, typically reorienting the magnetic moments and spin axes of the nuclei away from their initial orientation in the biasing field. Following a pulse that reorients the magnetic moments of adjacent nuclei, the nuclei relax over a period of time ($T_1$) and return to their original alignment relative to the biasing field. This time describes the return to equilibrium magnetization in the longitudinal direction and is called the spin-lattice relaxation time. The specific time period varies with the type of nuclei, the incident magnetic fields, and the amplitude of the excitation.

In addition, adjacent nuclei of the same element, subjected locally to the same biasing field, gradient field, and excitation conditions, have magnetic moments that tend to process synchronously, in phase with one another, which persists for a limited time after the excitation is discontinued. The phase synchronized spins of a group of adjacent nuclei together produce a detectable signal at the resonant frequency. When the phases are random, the net emitted signal is zero. Thus, the amplitude of the signal varies with the concentration of nuclei that are processing in phase. The signal decays over a period of time ($T_2$) as the nuclei fall out of phase with one another. This time describes the return to equilibrium of the transverse magnetization and is called the spin-spin relaxation time. This time period is related to the type of nuclei, the bias conditions, excitation, and the temperature of the sample being imaged.

An echo decay experiment is often used to measure this $T_2$ decay constant. Pulse sequences are designed to include pulses that are synchronous with nuclei of a particular element and/or that affect the precession and phase relationships of adjacent nuclei. Signals are received along a phase encoding axis and are sampled, digitized, and processed by Fourier transforms to convert so-called k-space data to spatially resolved amplitude data. The resulting values can distinguish the nuclei of one element from another in a three-dimensional matrix of voxel locations. The values are stored in a memory referenced to spatial location in the imaged volume and can be displayed in slices or projections, enabling the practitioner to visualize the tissues based on the detected concentrations of elements therein.

MRI visualization is based on measuring differences in $T_1$ and $T_2$ decay (and derivatives thereof) resulting from differences in the amount of water and/or salts, ions, elements, macromolecules, etc. in tissues throughout the volume analyzed. However, when a difference in intensity caused by the contrast between different tissues (or between healthy and diseased tissues) is not sufficient to obtain satisfactory clinical information, MRI contrast agents are used to improve visualization.

A contrast agent is a substance that, when administered to a subject, increases the image contrast (e.g., provides contrast enhancement) between a chosen target, tissue, or organ and the rest of the field of the image (e.g., the remaining areas of the body), or between healthy and diseased tissues. Contrast agents possess permanent magnetic dipoles, which influence the relaxation processes of the nearby water protons and so lead to a local change of the image contrast. In particular, the relaxation rates of water in body tissue may be increased by adding paramagnetic metal ions (ions with unpaired electrons) to the tissue. The unpaired electrons in these metals greatly increase the relaxation rates of nearby water protons. Thus, where paramagnetic metals are taken up in a greater amount by certain tissues, the relaxation rates of water protons in those tissues are increased relative to tissues that take up a lesser amount of the metal. These tissues appear light in MRI images. A substance, such as one of these paramagnetic metals, which causes tissue to appear lighter or darker in MRI images as a result of its presence is termed a contrast agent. Desirable properties for a contrast agent include high relaxivity, low toxicity, and the ability to distinguish different tissues or pathologies. Gadolinium (which causes a decrease in signal on $T_2$-weighted images and an increase in signal on $T_1$-weighted images) and superparamagnetic iron-oxide (which improves tumor contrast by decreasing the $T_2$ signal in normal tissue) are known conventional contrast agents.

Contrast agents can be introduced to improve the extent to which pertinent tissue types and tissue structures can be distinguished, in particular because the contrast agents assume different concentrations in different tissues. For example, vascular contrast agents improve the visualization of the vascular system by altering the contrast of the vascular system relative to the surrounding tissues, usually by brightening (hyper-intensifying) the vascular system (e.g., the blood). In addition, tissues also can be distinguished with respect to differences in the rates at which a perfused contrast agent diffuses into the tissues and the image contrast obtained by the contrast agent fades away in successive MR images taken over a period of time. Moreover, some contrast agents are responsive to the physical environment (e.g., pH, calcium ion concentration, temperature) or to biomolecular markers (e.g., an antibody, a nucleic acid, a protein, a metabolite, hemoglobin, choline, creatine, lactate, etc.) present in biological systems.

MRI using a contrast agent is a grayscale technique, e.g., it results in the visualization of variations along a one-dimensional continuum of intensities. However, because MRI is prone to imaging artifacts and many factors influence image intensity, contrast interpretation on MRI molecular imaging is difficult. The art would benefit from MR imaging in multiple colors that increases the information content of the MRI image, and thus improves the diagnostic power of the technique.

Compared to conventional technologies that assign colors to tissues, colorizing contrast agents has presented unique challenges in the art because many properties that influence signal intensity, such as $T_1$ and $T_2$, vary with concentration and contrast agent localization. In addition, distinguishing different contrast agents that are co-localized is another challenge because the agents work by influencing their molecular environment without emitting an intrinsic signal.

SUMMARY

Provided herein is technology relating to magnetic resonance imaging contrast agents and particularly, but not exclusively, to methods and systems for visualizing one or more magnetic resonance imaging contrast agent.

MBI uniquely enables the multiplexing, quantitation, and specific detection of MRI contrast agents, conferring on them the advantages that were once exclusive to optical and nuclear imaging. The framework, when implemented fully, will remove a significant barrier towards the routine use of molecular MRI and opens new possibilities for contrast agent design, biomarker quantitation, and multi-marker detection of pathologies.

For example, in some embodiments, provided herein is a method of visualizing a contrast agent by magnetic resonance imaging, the method comprising: a) imaging at least one contrast agent to generate $T_1$, $T_2$, and $T_2^*$, and quantitative susceptibility maps; b) processing the maps using a machine learning algorithm trained to recognize the contrast agent; and b) generating quantitative maps of the contrast agent concentration, identity, and functional state. In some embodiments, the processing step further comprises a pre-processing step. In some embodiments, the machine learning algorithm comprises radial basis function neural network training. In some embodiments, the at least one contrast agent is at least two contrast agents and each of the agents are represented by different colors on the quantitative maps. In some embodiments, different states of the same contrast agent are represented by different colors on the quantitative maps. In some embodiments, the contrast agent is one or more of Gd(III)-daa, Gd(III) biotin, Feridex, MPIO, or super paramagnetic iron oxide (SPIO). In some embodiments, the contrast agent binds to a molecular marker. In some embodiments, the method comprises imaging a tissue or plurality of tissues in vivo or in vitro. In some embodiments, the magnetic resonance imaging is multimodal imaging (e.g., PET-MRI or SPECT-MRI). In some embodiments, the method further generates one or more of background removal, unambiguous detection of smart agent activation, or targeted agent binding events. In some embodiments, the maps are generated using a pulse sequence or combination of 2 (e.g., 2, 3, 4, or more) sequences selected from, for example, rapid acquisition with refocused echoes (RARE), multi-Spin echo (MSE) pulse sequence, multi-gradient echo (MGE), T1rho mapping, intermolecular multiple quantum coherences, ultrashort echo time relaxometry, or dispersion imaging.

Further embodiments provide a system for visualizing a contrast agent by magnetic resonance imaging, the system comprising: a) at least one contrast agent; and b) computer software and a computer processor configured to collect images of said at least one contrast agent, generate $T_1$, $T_2$, and $T_2^*$, and quantitative susceptibility maps, process the maps using a machine learning algorithm trained to recognize the contrast agent; and generate quantitative maps of the contrast agent concentration, identity, and functional state.

Additional embodiments are described herein.

BRIEF DESCRIPTION OF THE DRAWINGS

These and other features, aspects, and advantages of the present technology will become better understood with regard to the following drawings.

DETAILED DESCRIPTION

Provided herein is technology relating to magnetic resonance imaging contrast agents and particularly, but not exclusively, to methods and systems for visualizing one or more magnetic resonance imaging contrast agent. The technology comprises collecting MM data for contrast agents in vitro and using pattern recognition to define a magnetic barcode for the contrast agent.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "subject" means any organism. The term need not refer exclusively to a human being, one example of a subject, but can also refer to animals such as mice, rats, dogs, poultry, and *Drosophila* and even tissue cultures. The technology disclosed herein is particularly useful in the diagnosis and treatment of warm-blooded vertebrates. Thus, the disclosure concerns mammals and birds. More particularly, the methods relate to the diagnosis and/or treatment of mammals such as humans, as well as those mammals of importance due to being endangered (such as Siberian tigers), of economical importance (animals raised on farms for consumption by humans), and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. The technology also relates to subjects that are birds, including those kinds of birds that are endangered, kept in zoos, as well as fowl, and more particularly domesticated fowl, e.g., poultry, such as turkeys, chickens, ducks, geese, guinea fowl, and the like, as they are also of economical importance to humans.

As defined herein, a "tissue" is an aggregate of cells that perform a particular function in an organism. The term "tissue" as used herein refers to cellular material from a particular physiological region. The cells in a particular tissue may comprise several different cell types. A non-limiting example of this would be brain tissue that further comprises neurons and glial cells, as well as capillary endothelial cells, and blood cells. The term "tissue" also is intended to encompass a plurality of cells that may normally exist as independent or non-adherent cells in the organism, for example, immune cells or blood cells. The term is further intended to encompass cell lines and other sources of cellular material that represent specific tissue types (e.g., by virtue of expression of biomolecules characteristic of specific tissue types).

As used herein the term "magnetic resonance (MR)" refers to the absorption or emission of energy by certain atomic nuclei in an external magnetic field after the application of RF excitation pulses using frequencies that satisfy the conditions of the Larmor equation (e.g., describing the precession of the magnetic moments of electrons, atomic nuclei, and atoms about an external magnetic field).

As used herein the term "MR imaging" or "MRI" refers to the use of magnetic resonance principles in the production of diagnostic views of a subject or sample where the resulting image is based upon three basic parameters (proton density, $T_1$ relaxation time, and $T_2$ relaxation time). A "magnetic resonance image" or "MR image" is referred to as "image space". Its Fourier transform is referred to as being "k-space". In magnetic resonance imaging, "k-space" is equivalent to the space defined by the frequency and phase encoding directions.

As used herein the term "contrast" refers to the relative difference of signal intensities in two adjacent regions of an image. Image contrast is dependent on the imaging technique and is associated with such parameters as proton density and $T_1$ or $T_2$ relaxation times.

As used herein the term "excitation" means delivering (inducing, transferring) energy into the "spinning" nuclei via radio-frequency pulse(s), which promotes the nuclei into a higher energy state. By producing a net transverse magnetization, a magnetic resonance imaging system can observe a response from the excited system.

As used herein the term "hydrogen density" or "proton density" refers to the concentration of hydrogen atoms or protons in water molecules or in some groups of fat molecules within tissue. Initial MRI signal amplitudes are directly related to $H^+$ density in the tissue being imaged.

As used herein, the term "relaxation time" refers to the time required for a nucleus that has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and $T_2$. $T_1$ is referred to as the longitudinal relaxation time and $T_2$ is referred to as the transverse relaxation time. Other relaxation times of relevance include, but are not limited to $T_{xp}$ (the paramagnetic contribution to the longitudinal relaxation rate) and $T_2^*$ (the transverse relaxation time including the effect of $B_o$ inhomogeneity). As used herein, the term "relaxation time" refers to the above-described relaxation times either together or in the alternative. Other relevant relaxation times will be apparent to those of skill in the art. A treatise on nuclear relaxation is available in, e.g., Banci, L, et al. *Nuclear and Electron Relaxation*, Verlag, Weinheim, 1991, which is herein incorporated by reference. As used herein the term "longitudinal relaxation time" refers to the time constant, $T_1$, which determines the rate at which excited protons return to equilibrium within the lattice or a measure of the time taken for spinning protons to re-align with the external magnetic field. The magnetization will grow after excitation from zero to a value of about 63% of its final value in a time of $T_1$.

As used herein the term "transverse relaxation time" refers to the time constant $T_2$, which determines the rate at which excited protons go out of phase with each other. $T_2$ is a measure of the time for spinning protons to lose phase coherence among the nuclei spinning perpendicular to the main field due to interactions among spins, resulting in a reduction in the transverse magnetization. The transverse magnetization value will decrease to a value of about 37% of its original value in a time of $T_2$.

As used herein the term "transverse relaxation time including the effect of $B_o$ inhomogeneity" refers to the time constant, $T_2^*$, that describes the loss of signal due to the dephasing of nuclei due to magnetic field inhomogeneity produced by minor differences in the chemical environment.

As used herein the term "paramagnetic substance" refers to a substance with weak magnetic properties, typically due to its unpaired electrons.

As used herein the term "proton density" refers to the concentration of mobile hydrogen atoms within a subject, sample, specimen, or tissue.

As used herein the term "proton density weighted image" refers to an image produced by controlling the selection of scan parameters to minimize the effects of $T_1$ and $T_2$, resulting in an image dependent primarily on the density of protons in the imaging volume.

As used herein the term "$T_1$ weighted image" refers to an image produced by controlling the selection of scan parameters to minimize the effects of $T_2$, resulting in an image dependent primarily on $T_1$.

As used herein the term "$T_2$ weighted image" refers to an image produced by controlling the selection of scan parameters to minimize the effects of $T_1$ and proton density, resulting in an image dependent primarily on $T_2$.

As used herein the term "pulse programmer" refers to the computer-controlled component of the MRI scanner that determines the timing of the pulse sequence parameters of the scan, such as echo time, pulse amplitude, phase, and frequency.

As used herein the term "pulse sequence" refers to a preselected set of defined RF and gradient pulses, usually repeated many times during a scan, wherein the time interval between pulses and the amplitude and shape of the gradient waveforms will control signal reception and affect the characteristics of the MR images.

As used herein the term "radio frequency" ("RF") refers to an electromagnetic wave with a frequency that is in the same general range as that used for the transmission of radio and television signals. The RF pulses used in MRI are commonly in the 1-100 megahertz range.

As used herein the term "readout gradient" refers to a magnetic field gradient applied during the period when the receiver components are on. The application of this gradient results in the frequency encoding of the object being imaged.

As used herein the term "receiver" refers to the portion of the MRI equipment that detects and amplifies the RF signals picked up by the receiver coil. Such equipment includes a preamplifier, signal amplifier, and demodulator.

As used herein the term "reconstruction" refers to the mathematical process by which the displayed image is produced from the raw k-space data obtained from the receiver circuitry, typically utilizing Fourier transformation and selective filtering.

As use herein the term "repetition time" ("$T_R$") refers to the amount of time that exists between successive pulse sequences applied to the same slice. It is delineated by initiating the first RF pulse of the sequence then repeating the same RF pulse at a time t. Variations in the value of $T_R$ have an important effect on the control of image contrast characteristics. Short values of $T_R$ (<1000 ms) are common in spin echo images exhibiting $T_1$ contrast and long values of $T_R$ (>1500 ms) are common in images exhibiting $T_2$ contrast.

As used herein, the term "echo time" ("$T_E$") refers to the amount of time allowed for decay from an initial maximum value to occur (e.g., for a spin echo or inversion recovery pulse sequence, the echo time is the time between the initial 90° RF pulse and the detection of the spin echo).

As used in this application, the term "computer component" refers to a computer-related entity, e.g., hardware, firmware, software, a combination thereof, or software in execution. For example, a computer component can be, but is not limited to being, a process running on a processor, a processor, an object, an executable, a thread of execution, a program, and a computer. By way of illustration, both an application running on a server and the server can be computer components. One or more computer components can reside within a process and/or thread of execution and a computer component can be localized on one computer and/or distributed between two or more computers.

"Logic", as used herein, includes but is not limited to hardware, firmware, software and/or combinations of each to perform a function(s) or an action(s). For example, based on a desired application or needs, logic may include a software controlled microprocessor, discrete logic such as an application specific integrated circuit (ASIC), or other programmed logic device. Logic may also be fully embodied as software.

"Software", as used herein, includes but is not limited to, one or more computer readable and/or executable instructions that cause a computer or other electronic device to perform functions, actions and/or behave in a desired manner. The instructions may be embodied in various fauns like routines, algorithms, modules, methods, threads, and/or programs. Software may also be implemented in a variety of executable and/or loadable forms including, but not limited to, a stand-alone program, a function call (local and/or remote), a servelet, an applet, instructions stored in a memory, part of an operating system or browser, and the like. It is to be appreciated that the computer readable and/or executable instructions can be located in one computer component and/or distributed between or among two or more, communicating, co-operating, and/or parallel processing computer components and thus can be loaded and/or executed in serial, parallel, massively parallel, and other manners. It will be appreciated by one of ordinary skill in the art that the form of software may be dependent on, for example, requirements of a desired application, the environment in which it runs, and/or the desires of a designer/programmer or the like.

As used herein, "k-means clustering" or "k-clustering" refers to a method of cluster analysis that partitions n observations into k clusters in which each observation belongs to the cluster with the nearest mean.

DETAILED DESCRIPTION

Provided herein is technology relating to magnetic resonance imaging contrast agents and particularly, but not exclusively, to methods and systems for visualizing one or more magnetic resonance imaging contrast agent.

Experiments described herein demonstrated a magnetic barcoding framework across a range of targeted, bio-responsive, gadolinium, and iron oxide contrast agents. By abandoning the treatment of T1 and T2 as a dichotomy, barcoding opens up several opportunities for MR contrast agent design. For example, an emerging strategy to enable quantitation and specific detection in molecular MRI is to synthesize multimodal probes (Frullano et al., Angew Chem Int Ed 2010; 49(13):2382-2384; Frullano L, Meade T J. Journal of Biological Inorganic Chemistry 2007; 12(7):939-949). Magnetic barcode imaging (MBI) helps to achieve the same goal while allowing the contrast agent design to remain simple. Another burdensome task in traditional contrast agent development is its optimization for different field strengths. MBI alleviates this need as evidenced by its successful detection of Gd(III)-biotin binding at 7 T even though the agent was optimized for 1.5 T and lost its property of binding-induced r1 enhancement at the higher field strength. Further opportunities lie in the parameter-tuning of contrast agents. MBI turns the old design rule of maximizing or minimizing r1/r2 ratio upside down as sensitivity and specificity are maximized with a balanced ratio in a multi-parameter framework. Similarly, engineering the traditionally ignored r2* becomes valuable in MBI because it adds a dimension to barcode space, as shown by MPIO. These properties indicate that the performance of MBI is further optimized when matched to specifically designed contrast agents.

In some embodiments, acceleration is provided to allow scan times on the order of a minute. Incorporation of compressed sensing (Lustig M, et al., Magn Reson Med 2007; 58(6):1182-1195), steady-state free precession (Deoni S C, et al., Magn Reson Med 2005; 53(1):237-241), or parallel imaging (Pruessmann K P, et al., Magn Reson Med 1999; 42(5):952-962) can shorten scan times by a factor of between 10-100 fold.

In some embodiments, the account for the increased number of combinations in vivo compared to in phantoms, the training set used for machine learning is expanded. One way to perform the expansion is to computationally add the relaxation rates and susceptibilities of blank tissues to those of the contrast agents; alternatively, training can be performed by imaging a collection of contrast-infused tissues ex vivo. The likelihood of such a change depends on the barcode design, the contrast agent used, the compartmentalization of the contrast agent, and tissue properties such as diffusion. Therefore, the extensiveness and the method of MBI training vary with the imaging problem being addressed. Another strategy for addressing complexity is to exploit pulse sequences that are more sensitive to magnetic materials than tissues, such as QSM or off-resonance imaging (Sherry A D, Woods M. Annu Rev Biomed Eng 2008; 10:391; Khemtong C, et al., Cancer Res 2009; 69(4):1651-1658). This strategy circumvents the more cumbersome method of acquiring pre-scans for background removal, and illustrates the unique opportunities to innovate in multi-parameter contrast agent imaging that is distinct from the challenges of tissue imaging.

MBI is a framework for integrating multi-dimensional image data into an output with emergent attributes that are highly desirable in a molecular imaging study. The use of machine learning circumvents the challenge of having to reinvent image analysis every time a new parameter is added to the acquisition. Pulse sequences such as T1ρ mapping (Wheaton A J, et al., Magn Reson Med 2004; 52(6):1453-1458), intermolecular multiple quantum coherences (Warren W S, et al., Science 1998; 281(5374):247-2514), ultrashort echo time relaxometry (Liu W, et al., Magn Reson Med 2009; 61(4):761-766), and dispersion imaging (Alford J K, et al., Magn Reson Med 2009; 61(4):796-802), can be employed under the MBI framework to further improve multiplexing degree, sensitivity, and accuracy. Similarly, signal intensities rather than fitted parameters can be explored as barcode components; this type of implementation has the advantage of improved accuracy when there are heterogeneous tissue types within a voxel. Furthermore, a wide array of machine learning (Liaw A, et al., R News 2002; 2(3):18-22; Suykens J A, et al., Neural Process Lett 1999; 9(3):293-300; Wu X, et al., Knowl Inf Syst 2008; 14(1):1-37) and susceptibility mapping algorithms (Liu J, et al., Neuroimage 2012; 59(3):2560-2568; Liu T, et al., Magn Reson Med 2013; 69(2):467-476; Liu T, et al., Magn Reson Imaging 2010; 28(9):1383-1389) exist that can be applied within the MBI framework to reduce processing artifacts and improve quantitation and classification accuracy. As an example, in the current implementation, the quantitative maps produced are multiplicative products of concentration and Bayesian probability. That is, voxels with low classification confidence display underestimated concentrations in exchange for fewer false positives. In the dataset, the largest underestimation seen is with the SPIOs at 15%, while the false positive rate as determined by the percentage of voxels with grossly over-estimated concentrations is <10%. This type of trade-off can be modified by the processing algorithm design.

For example, in some embodiments, provided herein is a method or system of visualizing a contrast agent by magnetic resonance imaging, the method comprising: a) imaging at least one contrast agent to generate $T_1$, $T_2$, and $T_2^*$, and quantitative susceptibility maps; b) processing the maps using a machine learning algorithm trained to recognize the contrast agent; and b) generating quantitative maps of the contrast agent concentration, identity, and functional state. In some embodiments, the processing step further comprises a pre-processing step. In some embodiments, the machine learning algorithm comprises radial basis function neural network training. In some embodiments, the at least one contrast agent is at least two contrast agents and each of the agents are represented by different colors on the quantitative maps. In some embodiments, different states of the same contrast agent are represented by different colors on the quantitative maps. In some embodiments, the contrast agent is one or more of Gd(III)-daa, Gd(III) biotin, Feridex, MPIO, or super paramagnetic iron oxide (SPIO). In some embodiments, the contrast agent binds to a molecular marker. In some embodiments, the method comprises imaging a tissue or plurality of tissues in vivo or in vitro. In some embodiments, no radioactive agents are utilized in the methods, thus avoiding added risk to users.

The systems and methods described herein utilize a combination of multiple MR pulse sequences (e.g., a CPMG sequence to measure T2 and another to measure susceptibility), although other pulse sequence are specifically contemplated. Examples include, but are not limited to, T1rho mapping, intermolecular multiple quantum coherences, ultrashort echo time relaxometry, and dispersion imaging. In some embodiments, ultrashort echo time sequences are substituted for the T2 and T2star sequences. In some embodiments, the combination of pulse sequences is optimized to the contrast agent being imaged. For example, when imaging gadolinium agents, T2star is not required, but it adds useful information when imaging iron agents.

The systems and methods described herein provide one or more of an estimation of contrast agent concentration, background removal, unambiguous detection of smart agent activation and targeted agent binding event, and multiplexing. These functions are all key features of MBI are made possible by the use of multiple MR pulse sequences.

Exemplary embodiments described herein utilize neural networks. However, other machine learning algorithms can also be utilized in the described methods.

MRI Apparatus

MRI employs a magnetic field, radio frequency energy, and magnetic field gradients to make images of the body. The contrast or signal intensity differences between tissues mainly reflect the $T_1$ (longitudinal) and $T_2$ (transverse) relaxation values and the proton density (effectively, the free water content) of the tissues. In changing the signal intensity in a region of a patient by the use of a contrast agent, several possible approaches are available. For example, a contrast medium can be used to change the $T_1$, the $T_2$, or the proton density of the tissue which contains the contrast agent.

A typical MRI apparatus includes a basic field magnet supplied by a basic field magnet supply. The system has gradient coils (operated by a gradient coils supply) for emitting gradient magnetic fields. An RF antenna is provided for generating the RF pulses and for receiving the resulting magnetic resonance signals from a subject or sample being imaged and/or a device inserted therein. The RF antenna is operated by an RF transmission/reception unit. The RF antenna may be employed for transmitting and receiving, or alternatively, separate coils can be employed for transmitting and receiving. The gradient coils supply and the RF transmission/reception unit are typically operated by a control computer to produce radio frequency pulses that are directed to the subject to be imaged. The magnetic resonance signals received from the RF antenna are subject to a transformation process, e.g., a two-dimensional fast Fourier transform (FFT), which generates pixelated image data. The transformation may be performed by an image computer or other similar processing device. The image data may then be shown on a display. The image data may include images of both the subject or sample to be imaged and an inserted device or object.

The systems and methods described herein find use in a variety of MRI applications. Examples include, but are not limited to, single mode MRI and multi-modal combinations of MRI and other imaging modalities (e.g., PET-MRI and SPECT-MRI). Magnetic barcode imaging (MBI) helps to achieve the same goal while allowing the contrast agent design to remain simple, and as such, MBI finds use in multi-modal imaging techniques.

Positron emission tomography (PET) is a nuclear medicine functional imaging technique that is used to observe metabolic processes in the body. The system detects pairs of gamma rays emitted indirectly by a positron-emitting radionuclide (tracer), which is introduced into the body on a biologically active molecule. Three-dimensional images of tracer concentration within the body are then constructed by computer analysis. In modern PET-CT scanners, three dimensional imaging is often accomplished with the aid of a CT X-ray scan performed on the patient during the same session, in the same machine.

Single-photon emission computed tomography (SPECT) is a nuclear medicine tomographic imaging technique using gamma rays. It is very similar to conventional nuclear medicine planar imaging using a gamma camera (that is, scintigraphy). However, it is able to provide true 3D information. This information is typically presented as cross-sectional slices through the patient, but can be freely reformatted or manipulated as required.

The technique utilizes delivery of a gamma-emitting radioisotope (a radionuclide) into the patient, normally through injection into the bloodstream. On occasion, the radioisotope is a simple soluble dissolved ion, such as an isotope of gallium(III). Most of the time, though, a marker radioisotope is attached to a specific ligand to create a radioligand, whose properties bind it to certain types of tissues.

Contrast Agents

In MRI, the contrast in the generated image may be enhanced by introducing into the subject or sample (e.g., an area of the body or a tissue) being imaged an agent (a "contrast agent"). A contrast agent affects the spin reequilibration characteristics of nuclei (the "imaging nuclei" which generally are protons and more especially water protons) that are responsible for the resonance signals from which the images are generated. The enhanced contrast thus obtained enables particular organs or tissues to be visualized more clearly by increasing or by decreasing the brightness of the image of the particular organ or tissue relative to that of its surroundings.

Paramagnetic contrast agents contain unpaired electrons that act as small local magnets within the main magnetic field to increase the rate of longitudinal ($T_1$) and transverse ($T_2$) relaxation. At concentrations normally used in MRI, most paramagnetic contrast agents have their predominant effect on $T_1$ relaxation. Most paramagnetic contrast agents are metal ions (e.g., gadolinium) that in most cases are toxic. To decrease the toxicity of these metals, the metal ions are generally chelated using ligands. The resultant paramagnetic metal ion complexes have decreased toxicity. Nitroxides are another class of MRI contrast agent that is also paramagnetic. These have relatively low relaxivity and are generally less effective than paramagnetic ions as MRI contrast agents.

Gadolinium(III) MRI contrast agents (e.g., typically as a chelated complex) are the most commonly used contrast agents, e.g., for the enhancement of blood vessels and or to image brain tumors that cause degradation of the blood-brain barrier. For large blood vessels (e.g., the aorta and its major branches), the gadolinium(III) dose can be as low as 0.1 mmol/kg body mass. Higher concentrations are often used for finer vasculature. Gd(III) chelates do not pass the blood-brain barrier because they are hydrophilic. Thus, these are useful in enhancing lesions and tumors where the Gd(III) leaks out. In the rest of the body, the Gd(III) initially remains in the circulation but then distributes into the interstitial space or is eliminated by the kidneys.

Metal oxides, most notably iron oxides, have also been tested as MRI contrast agents. Two types of iron oxide contrast agents exist: superparamagnetic iron oxide (SPIO) and ultrasmall superparamagnetic iron oxide (USPIO). While small particles of iron oxide, e.g., under 20 nm diameter, may have paramagnetic relaxation properties, their predominant effect is through bulk susceptibility. These contrast agents consist of suspended colloids of iron oxide nanoparticles and when used during imaging reduce the $T_2$ signals of absorbing tissues. SPIO and USPIO contrast agents have been used successfully in some instances for liver tumor enhancement.

Some superparamagnetic iron platinum particles (SIPPs) have better $T_2$ relaxivities compared with iron oxide nanoparticles. In some embodiments, SIPPs are encapsulated with phospholipids to create multifunctional SIPP "stealth" immunomicelles, e.g., that specifically target human prostate cancer cells.

Manganese chelates such as Mn-DPDP enhance the $T_1$ signal and have been used for the detection of liver lesions. Manganese ions ($Mn^{2+}$) are often used as a contrast agent in animal studies, usually referred to as MEMRI (Manganese Enhanced MRI). $Mn^{2+}$ enters cells through calcium channels, and thus facilitates functional brain imaging.

SPIO, barium sulfate, air, and clay also lower $T_2$. Some natural products with high manganese concentration (e.g., blueberries and green tea) are sometimes used to increase $T_1$ contrast. Some perfluorocarbons have been used as gastrointestinal MRI contrast agents. These contrast agents work by reducing the amount of protons in a body cavity, thus causing it to appear dark in the images.

Although the disclosure herein refers to certain illustrated embodiments, it is to be understood that these embodiments are presented by way of example and not by way of limitation.

EXAMPLES

Example 1

Methods

Contrast Agents

Gd(III)-daa was synthesized using a previously described protocol (Matosziuk L M, et al., Inorg Chem 2013; 52(21): 12250-12261). The version of Gd(III)-daa used has a 5-carbon linker. Synthesis of Gd(III)-biotin employed the synthetic strategy described in (Harrison V S, et al., Chemical Communications 2014; 50(78):11469-11471) to achieve 3-(2,4,6)-Tris(1-2(hydroxyl-3-(1H-1,2,3-triazol-1-yl(propyl)-3,7,10-tris(carboxymethyl)-1,4,7,10-tetraazacyclodo-decylgadolinium(III)phenoxy)-propan-1-amine (C3-amine). C3-amine (1.6 mg, 0.0008 mmol) was suspended in 200 μL, pH 9.4 bicarbonate buffer under inert atmosphere. To the stirring solution was added biotin N-hydroxysuccinimide ester (Kimura Y, et al., Organic letters 2013; 15(16):4130-4133) (1.2 mg, 0.0035 mmol) dissolved in 100 μL of DMSO. After 24 hours, the solvent was removed by lyophilization and the product purified by reverse phase HPLC using a C18 column, held at 5% for 5 minutes and eluting with a gradient of 5% to 20% acetonitrile in pH 10.38 buffered water over 21 minutes, tr=11.8 minutes. This gave 1.1 mg of pure product as a white solid (55% yield). MS (MALDITOF): m/z observed=2250.2 [$M^+$], 2273.2 [$M^++Na^+$], 2289.2 [$M^++K^+$], 2312.2 [$M^++Na^++K^+$], m/z calculated=2250.5 [Mv], 2273.5 [$M^++Na^+$], 2289.5 [$M^++K^+$], 2312.5 [$M^++Na^++K^+$]. Super paramagnetic iron oxide SPIO was synthesized using a published method (27). The SPIO used was surface-functionalized with diethylene glycol. Feridex was purchased from Bayer HealthCare (Wayne, N.J.). MPIO was purchased from Bangs Laboratories (Cat. No. ME03F, Fishers, Ind.). Concentrations of agents were measured using ICP-MS. Iron oxide particle concentrations reported are Fe concentrations. Gd(III)-biotin concentrations reported are molecular concentrations. MPIO concentrations reported in μg/mL include polymeric weight and were based on supplier label.

Training Agarose Phantoms

All agarose phantoms used for radial basis function neural network (RBFNN) training were prepared in a similar fashion, consisting of contrast agent-doped 1% low melting point (lowMP) agarose (Life Technologies, Carlsbad, Calif.) embedded within blank 1% regular agarose. 2% agarose in milliQ water and a buffer were mixed in equal parts to produce 1% agarose. The buffer used was 10 mM HEPES for Gd(III)-daa, 10 mM PBS for Gd(III)-biotin, and milliQ water for SPIO, Feridex, and MPIO in the multiplexing experiment. MPIO training for the zero background experiment was performed using 10% serum-supplemented minimum essential media mixed with 2% agarose in equal parts (media-agarose). All samples were prepared in 15 mL conical tubes. 4 mL of 1% agarose was gelled at room temperature around a 5 mm OD NMR tube. The tube was later removed to create a cylindrical bore of approximately 1 cm in depth. The bore was filled with 220 μL of 1% low MP agarose doped with the appropriate concentration of contrast agent. Concentrations are specified in the methods of each individual experiment. After filling, the tube was cooled to 4° C. for 5 minutes to solidify the doped low MP agarose. To the same tube, 2 mL of 1% agarose was added and solidified for 5 minutes at 4° C. to completely enclose the doped lowMP agarose. Approximately 5 mL of the same buffer used to prepare the agarose was diluted to 10 mL with milliQ water and added on top of the agarose plug to completely fill the tube. Diffusion in agarose occurred for small molecule contrast agents.

Therefore, imaging was performed immediately after preparation of the phantom.

Magnetic Barcode Acquisition Imaging was performed at 25° C. on a Bruker Pharmscan 7 T imaging spectrometer equipped with shielded gradient coils (Bruker BioSpin, Billerica, Mass.). A 300 MHz 1H 89 mm/23 mm quadrature transceiver volume coil was used. The Bruker MapShim method was used for shimming. T1 measurements were performed using a Rapid Acquisition with Refocused Echoes (RARE) pulse sequence. T2 measurements were performed using a Multi-Spin Echo (MSE) pulse sequence. T2* measurements were performed using a Multi-Gradient Echo (MGE) pulse sequence. Field map measurements used for susceptibility mapping were performed using the Bruker FieldMap macro based on a double gradient echo pulse sequence. Unless otherwise specified, the geometries for T1, T2, and T2* acquisitions were FOV=15×15 mm2, slice thickness=0.9375 mm, and matrix=128×128. The parameters for field map acquisitions were TR=29.6 ms, TE=2.3, 27.1 ms, NEX=1, FOV=22.5×22.5×22.5 mm3, matrix size=96×96×96, and scan time=4 min 33 s. Other pulse sequence parameters are detailed in the methods for each individual experiment.

Barcode Processing and Machine Learning

T1 and T2 maps were generated using custom programs written in Matlab (version R2010b, MathWorks, Natick, Mass.). For T1, each voxel in a repetition time (TR) series of images was fitted to equation $S=M\cdot[1-\exp(-TR/T1)]$. S is signal, and M is equilibrium magnetization. S and TR were known. M and T1 were fitted. For T2, each voxel in an echo time (TE) series of images was fitted to equation $S=M\cdot\exp(-TE/T2)+C$. C is an arbitrary constant that is fitted. T2* was fitted in the same way as T2. Susceptibility maps were generated based on field maps using the Quantitative Susceptibility Mapping (QSM) algorithm described by de Rochefort, et al (de Rochefort L, et a., Magn Reson Med 2010; 63(1):194-206). Field map voxels with SNR<6 were set to 0. Regions-of-interest (ROI) were defined by the non-zero regions in the field map. Manual corrections were performed to include air bubbles within the sample into the ROI. Top and bottom 5 rows of the field maps were removed to minimize interference from field inhomogeneity during QSM processing. Tuning of the conjugate gradient loop stop criterion and the edge regularization parameter was performed manually; values that result in stable solutions that do not vary significantly with the parameters were selected. These parameters were kept the same across training and testing for each experiment. Procedures for automatic parameter selection are available (de Rochefort L, et al., Magn Reson Med 2010; 63(1):194-206) but were not implemented. RBFNN training and image processing were performed in Matlab using the neural network toolbox. 200 voxels from each training agarose phantom were randomly selected and aggregated to form the training set for each contrast agent or agent functional state. For Gd(III)-daa and Gd(III)-biotin, 200 additional training data points were generated by interpolation to provide coverage for partial Gd(III)-daa activation and partial Gd(III)-biotin binding. Each training set was normalized by its own mean and standard deviation. An empirical relationship between susceptibility, as obtained by QSM, and concentration, as measured by ICP-MS, was then found by linear fitting. The empirical equation was used to calculate the answer vector containing concentrations for multivariate regression training. The number of nodes in the RBFNN was restricted to less than 500. A spread of 0.1-0.3 and a mean error goal of <10% were used.

Relaxivity and Susceptibility Measurement

The r1, r2, and r2* of contrast agents were obtained from their respective training set. From the T1, T2, and T2* maps of each agent at each concentration, the relaxation time values were recorded from voxels near the center of the agarose phantom to minimize errors introduced by agent diffusion. r1, r2, and r2* were found as the slopes of linear fits of 1/T1, 1/T2, and 1/T2*, respectively, against concentration in units of mM-1s-1. The $\chi M$ of each agent was obtained in a fashion similar to how relaxivities were measured, except that $\chi M$ was found as the slope of $\chi$ linearly fitted against concentration in units of ppm/M. $\chi M$ were calibrated against the theoretical Gd(III) value of 326 ppm/M (29) using a calibration factor obtained by comparing the Gd(III)-daa data to the theoretical value.

Zero-Background Imaging

The test phantom was prepared in a 4 mL 15×45 mm glass vial. 2 mL of 1% media-agarose warmed at 70° C. was added to the vial. As the agarose gels, 10 µL of each of 8 µg/mL MPIO and 2.3 mM FeCl3 in 1% media-lowMP agarose warmed at 60° C. was carefully infused in two separate spots. Ten µL of dodecanol was infused in a third location. The 1% media-low MP agarose was colored by 2.5% v/v trypan blue for visibility. The sample was solidified for 5 minutes at 4° C. before 2 mL more of 1% media-agarose was added and cooled at 4° C. for 5 minutes. Media diluted 2× by milliQ water was added at the end to completely fill the vial. RBFNN training was performed using 0, 2, 4, 6, 8, 10 µg/mL MPIO. Detailed imaging parameters are as follows: for T1 measurements, TR=770, 1300, 1900, 2700, 3700, 5000, 7400, 17500 ms, effective TE=36 ms, RARE factor=8, NEX=1, and scan time=10 min 44 s. For T2 measurements, TR=3500 ms, TE=11, 22, 33 . . . 358 ms in 11 ms increments, NEX=1, and scan time=7 min 28 s. For T2* measurements, TR=3000 ms, TE=5, 13, 21 . . . 317 ms in 8 ms increments, matrix=256×256, NEX=1, and scan time=12 min 48 s. For T2-weighted imaging, TR=3500 ms, TE=88 ms, and NEX=1.

Bio-responsive and Targeted Agent Imaging

Test phantoms were prepared in a similar method as described for the training phantoms. An additional step was included for mixtures of Gd(III)-daa with ZnCl2, and Gd(III)-biotin with avidin (Molecular Probes Cat. No. A887, Eugene, Oreg.) or human serum albumin (Sigma-Aldrich Cat. No. A9511, St. Louis, Mo.). Specifically, these solutions were left undisturbed for 30 min at RT to ensure complete activation or binding before doping into lowMP agarose. Bioresponsive activation of Gd(III)-daa occurs when the diacetate domain binds Zn2+, opening a coordination site on the Gd(III) and concomitantly increasing r1 and r2. Gd(III)-biotin is targeted to avidin. When incubated with the protein, the tumbling rate of the agent decreases and its relaxivities change accordingly. For Gd(III)-daa, training was performed using 0, 0.25, 0.75, 1.25, 2 mM Gd(III)-daa with and without 2 equivalents of ZnCl2. For Gd(III)-biotin, training was performed using 0, 50, and 100 µM molecule without avidin, and 33.3, 66.7, 83.3 µM molecule with ⅓ equivalents of avidin. Detailed imaging parameters for Gd(III)-daa are as follows: for T1 measurements, TR=49, 57, 66, 75, 84, 94, 105, 117, 130, 145, 160, 175, 190, 210, 230, 260, 300, 350, 450, 750 ms, effective TE=9 ms, RARE factor=2, NEX=1, and scan time=4 min 15 s For T1-weighted imaging, TR=100 ms, TE=9 ms, RARE factor=1, and NEX=1. For T2 measurements, TR=800 ms, TE=11, 22, 33 . . . 358 ms in 11 ms increments, NEX=1, and scan time=1 min 42 s. Parameters for Gd(III)-biotin are as follows: for T1 measurements, TR=62, 72, 84, 104, 124, 144, 164, 190, 220, 250, 280, 320, 360, 400, 460, 520, 600, 700, 900, 1500 ms, effective TE=9 ms, RARE factor=2, NEX=1, and scan time=7 min 57 s. For T1-weighted imaging, TR=400 ms, TE=9 ms, RARE factor=1, and NEX=1. For T2 measurements, TR=800 ms, TE=11, 22, 33 . . . 358 ms in 11 ms increments, NEX=1, and scan time=1 min 42 s. Display intensities of the T1-weighted images were normalized by equalizing the blank agarose intensity across images.

Multiplexed Imaging

The test phantom was prepared in a 15 mL conical tube. 12 mL of 1% agarose was gelled at RT around five 16 gauge needles that were later removed to create cylindrical bores in the agarose. 1% low MP agarose warmed at 60° C. and doped with various concentrations of SPIO, Feridex, and MPIO were used to fill the cylindrical bores. Contrast agent concentrations are indicated in the relevant figure. The volume used for each bore was 25 µL. The sample was cooled at 4° C. for 5 min to solidify the low MP agarose. Two mL more of 1% agarose was added and solidified at 4° C. for 5 min to completely encapsulate the embedded contrast agent. The remainder of the tube was filled with milliQ water. RBFNN training was performed using 240 and 320 µM Fe SPIO, 60 and 80 µM Fe Feridex, 60 and 80 µM Fe MPIO, 120/30 and 160/40 µM Fe SPIO/Feridex mixture, and 120/30 and 160/40 µM Fe SPIO/MPIO mixture. Additionally, blank 1% agarose was included in the training set to define the zero point for regression training. Detailed imaging parameters are as follows: For T1 measurements, TR=315, 400, 480, 570, 650, 750, 850, 1000, 1100, 1200, 1400, 1600, 1800, 2000, 2300, 2600, 3000, 3500, 4400, and 7500 ms, effective TE=36 ms, RARE factor=8, NEX=1, and scan time=9 min 58 s. For T2 measurements, TR=3500 ms, TE=11, 22, 33 . . . 358 ms in 11 ms increments, NEX=1, and scan time=7 min 28 s. For T2* measurements, TR=3500 ms, TE=5, 13, 21 . . . 317 ms in 8 ms increments, NEX=1, and scan time=7 min 28 s. For T2-weighted imaging, TR=3500 ms, TE=176 ms, and NEX=1.

Results

Figure 1:
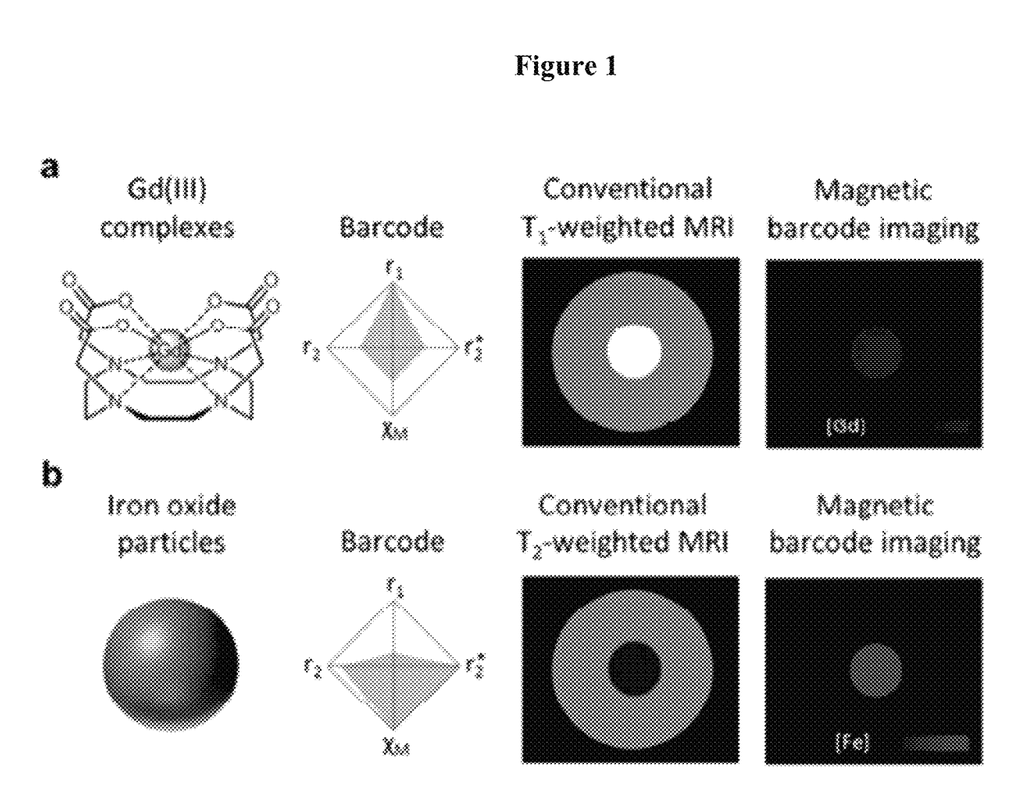
FIG. 1 shows magnetic barcode imaging. Conventional molecular MRI utilizes (a) T1-weighted imaging for gadolinium and (b) T2-weighted imaging for iron oxide.
Figure 2:
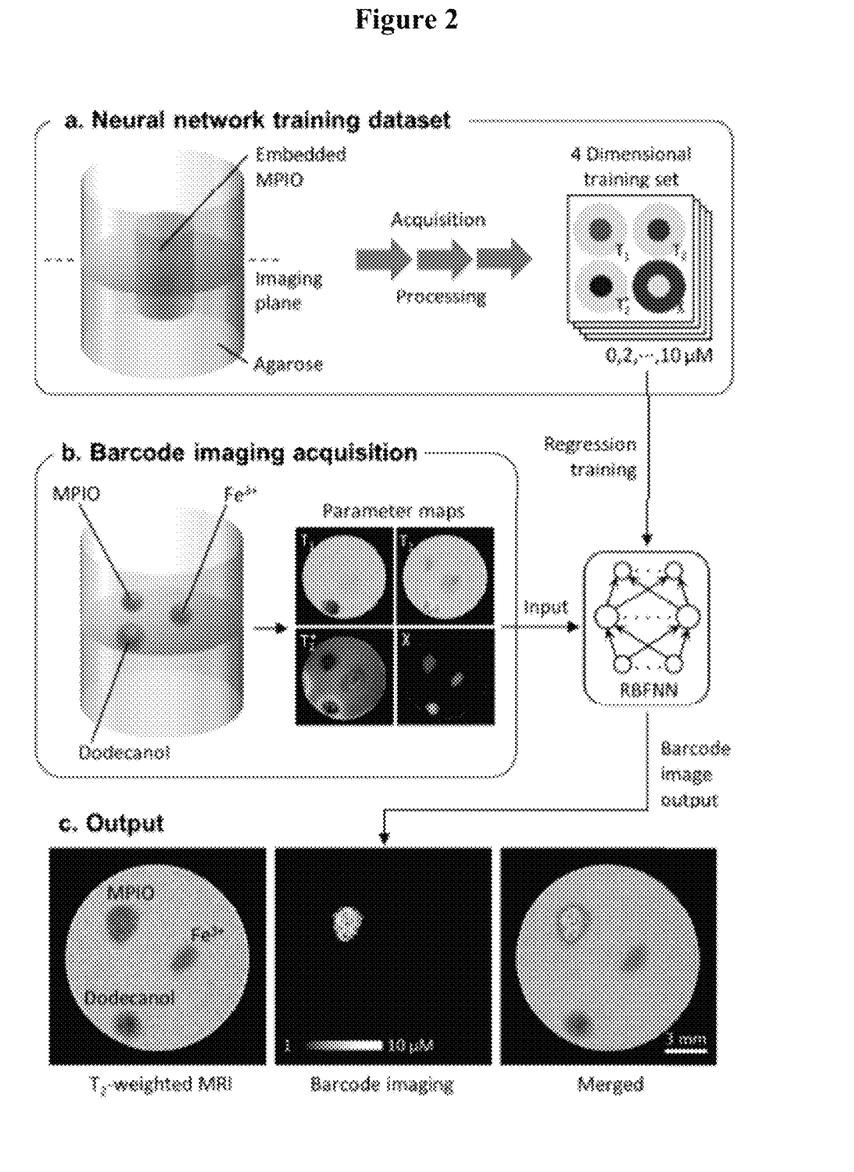
FIG. 2 shows implementation and zero-background imaging. (a) The RBFNN is trained to recognize MPIO using a 4-dimensional training set generated by imaging agarose phantoms doped with 0-10 µg/mL MPIO. (b) Zero-background imaging is tested by embedding 8 µg/mL MPIO, fat-mimicking dodecanol, and FeCl3 simulating a hemorrhage into agarose. (c) By T2-weighted MRI, the three hypo-intensities are indistinguishable.

MBI uniquely identifies contrast agents and their functional states by signatures that are encoded in the magnetic properties and the molecular dynamics of each agent. To capture these signatures, a MBI implementation is comprised of a selection of acquisition pulse sequences, a pre-processing protocol, and a machine learning strategy (FIG. 2). Together, these components determine the barcode space dimensionality, the accuracy and precision of the measured parameters, and the classification and quantitation accuracy. The implementation reported here uses multi-gradient echo and Carr-Purcell-Meiboom-Gill multi-spin echo sequences to measure T1, T2, T2*, and phase-based susceptibility ($\chi$) in a voxel-by-voxel manner (Bernstein M A, King K F, Zhou X J. Handbook of MRI pulse sequences: Elsevier; 2004). This combination of pulse sequences captures the corresponding agent relaxivities and molar susceptibility (r1, r2, r2*, $\chi M$). For pre-processing, relaxation times were estimated by least squares fitting to known signal equations, and susceptibility was obtained using a morphology enabled dipole inversion method devised by de Rochefort, et al. (de Rochefort L, et al., Magn Reson Med 2010; 63(1):194-206) Machine learning was performed by a radial basis function neural network (31) (RBFNN) trained on contrast agent phantoms prepared at a range of concentrations (FIG. 2a). RBFNN was chosen because it is amenable to training without negative examples, outputs posterior Bayesian probabilities, and handles regression problems well. Depending on the training set used, the RBFNN can learn to highlight a single contrast agent from the background, or use different colors to represent different agents or different functional states of a single agent. The different RBFNN configurations used to achieve the different outputs are described in the results for each experiment.

Zero-background Imaging

Micron-sized Superparamagnetic Iron Oxide Particles (MPIOs) are customarily used in T2-weighted MRI. These agents generate negative contrast that is often confounded by hypointense features such as air, hemorrhage, iron-rich tissues, or calcification (Shin T-H, et al., ACS nano 2014; 8(4):3393-3401). In theory, a RBFNN trained to recognize MPIOs would differentiate the contrast agent from the confounding features. To test this hypothesis, MBI was performed on an agarose phantom embedding 8 μg/mL MPIO, fat mimicking dodecanol, and 2.3 mM FeCl3 simulating a hemorrhage. Training of the RBFNN was performed using 0-10 μg/mL MPIO.

MBI successfully distinguished MPIO from dodecanol and Fe3+ whereas T2-weighted imaging showed all three as undifferentiated hypo-intensities (FIG. 2c). On MBI, the MPIO contrast is displayed as a quantitative intensity without background. MBI recapitulates the major advantages of quantitation and zero-background in nuclear imaging—considered the gold standard in clinical molecular imaging—without the radiation risk and at a higher resolution.

Detection of Bio-responsive Agent Activation

Figure 3:
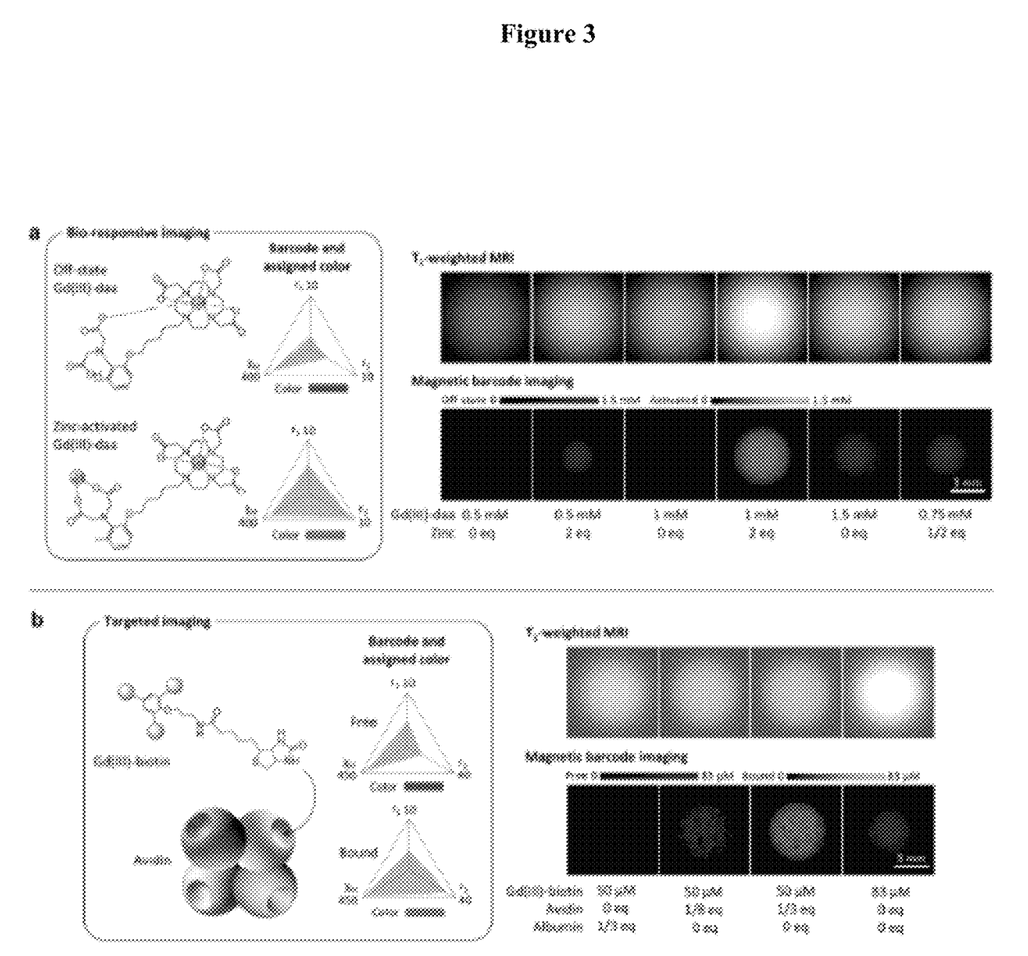
FIG. 3 shows color switching by functional state. (a) Gd(III)-daa is a Zn2+ sensor whose barcode increases in r1 and r2 upon Zn2+ binding. (b) Gd(III)-biotin is a targeted agent.

To test MBI on a bio-responsive agent, Gd(III)-diaminoacetate (Gd(III)-daa) was used as a model system. Gd(III)-daa is a $Zn^{2+}$ sensor that allows water coordination to Gd(III) upon $Zn^{2+}$ binding (Matosziuk L M, et al., Inorg Chem 2013; 52(21):12250-12261; Major J L, et al., Proc Natl Acad Sci USA 2007; 104(35):13881-13886). The binding event leads to an increase in the r1 and r2 to the agent's barcode (FIG. 3a). r2* is degenerate with r2 in Gd(III)-daa and not used. The RBFNN for this system was constructed with two output nodes to represent the concentrations of Gd(III)-daa in its off and activated state, respectively. The training performed on the agent was with and without $Zn^{2+}$ at a range of concentrations. Once the training was complete, testing was performed using concentrations not seen during training to demonstrate external validity.

The standard method for imaging bio-responsive Gd(III) agents is T1-weighted imaging. However, a major limitations of this method is evidenced by its inability to distinguish an activation event from an increase in agent concentration, as Gd(III)-daa produces residual contrast in its "off" (absence of Zn2+) state (FIG. 3a). MBI, on the other hand, unambiguously differentiates between the functional states of Gd(III)-daa regardless of concentration. Concentration is quantitatively displayed, allowing for the detection of partial activation when less than one equivalent Zn2+ is present. Therefore, MBI removes the obstacle of ambiguity in the imaging of Gd(III) bio-responsive agents.

Detection of Targeted Agent Binding

MBI can detect the binding of a targeted agent to the selected molecular target, analogous to the way differentiation is achieved with bio-responsive agent activation. To test this capability, an avidin-targeted agent (Gd(III)-biotin) was used. Using the same barcode design as Gd(III)-daa, Gd(III)-biotin phantoms with and without avidin across a range of concentrations were imaged for training. Upon Gd(III)-biotin binding to avidin, the molecular rotation slowed, decreasing r1 and increasing r2 (FIG. 3b). As before, testing was performed using concentrations that differ from those in the training set.

The goal of a targeted agent is to delineate the presence of a molecular marker from the background tissues. However, non-specific retention can compromise interpretation of the results. Under standard T1-weighted imaging, the binding status of the agent is unidentifiable (FIG. 3b). In comparison, MBI quantitatively displays the binding status of the contrast agent as a change in color by differentiating between the barcodes of the bound and unbound states. Further, MBI distinguishes between partial binding and saturation depending on whether Gd(III)-biotin or avidin is in excess. When human serum albumin instead of avidin was mixed with Gd(III)-biotin, MBI accurately identified the agent as unbound. The ability to switch color upon protein binding of a small molecule targeted contrast agent is a unique capability of MBI that has not been demonstrated with any other imaging modality.

Multiplexing of Iron Oxide Particles

Multiplexing in molecular imaging refers to the simultaneous visualization of multiple imaging agents (Gao X, et al., Nat Biotechnol 2004; 22(8):969-976). This capability is important because there is increasing realization that no single biomarker is likely to provide sufficient characterization of a disease process (Zavaleta C L, et al., Proc Natl Acad Sci USA 2009; 106(32):13511-13516).

Magnetic particles have the potential to serve as a platform for MR multiplexing because their magnetic and dynamic properties change with size, composition, and geometry (Lee J-H, et al., Nat Med 2006; 13(1):95-99). However, this potential has not been fully realized.

Figure 4:
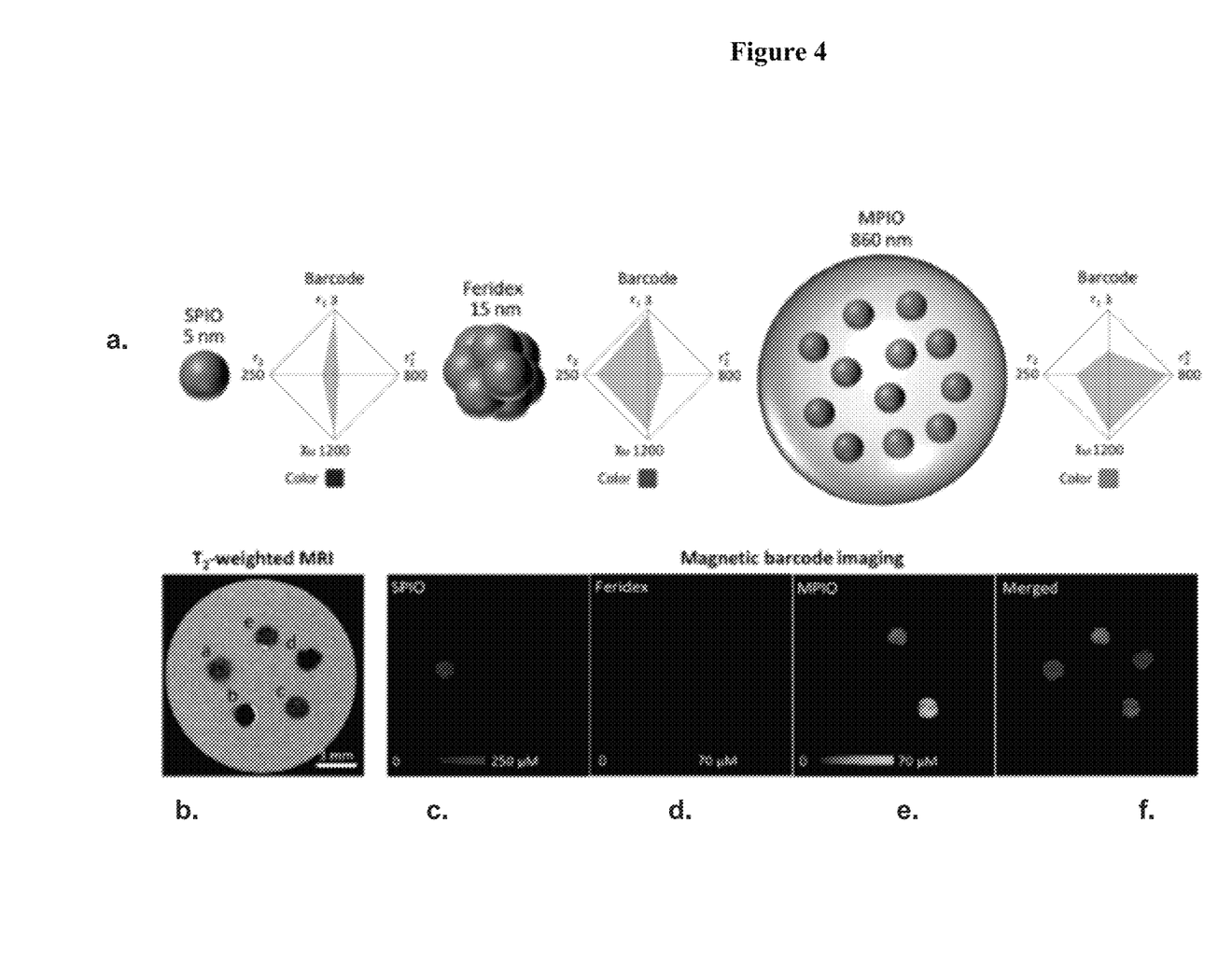
FIG. 4 shows multiplexing. (a) overview. (b) MRI overview. (c) 250 µM SPIO (d) 70 µM Feridex (e) 70 µM MPIO (f) merged

Using MBI, multiplexing was tested with superparamagnetic iron oxide nanoparticles (SPIOs), Feridex, and MPIOs. RBFNN training was performed on the individual particles as well as mixtures of particles. All three particles used were $Fe_3O_4$ in material, but of different sizes and configurations, producing distinct barcodes (FIG. 4). By T2-weighted MRI, the three particles embedded in agarose produce hypo-intensities that are indistinguishable from each other. When the same specimen is imaged by MBI, each particle is displayed as a different color on a quantitative scale, even in mixtures. This result supports the notion that magnetic particles can be multiplexed via the tuning of their size and shape.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in medical science, imaging, computer science, or related fields are intended to be within the scope of the following claims.

We claim:

1. A method of visualizing a contrast agent by magnetic resonance imaging, the method comprising:
   a) imaging at least one contrast agent to generate $T_1$, $T_2$, and $T_2^*$, and quantitative susceptibility maps;
   b) processing said maps using a machine learning algorithm trained to recognize said contrast agent to generate processed maps; and
   c) generating quantitative maps of said contrast agent concentration, identity, and functional state from said processed maps.

2. The method of claim 1, wherein said processing step further comprises a pre-processing step.

3. The method of claim 1, wherein said machine learning algorithm comprises radial basis function neural network training.

4. The method of claim 1, wherein said at least one contrast agent is at least two contrast agents and each of said agents are represented by different colors on said quantitative maps.

5. The method of claim 1, wherein different states of the same contrast agent are represented by different colors on said quantitative maps.

6. The method of claim 1, wherein said contrast agent is one or more of Gd(III)-daa, Gd(III) biotin, Feridex, MPIO, and super paramagnetic iron oxide SPIO.

7. The method of claim 1, wherein said contrast agent binds to a molecular marker.

8. The method of claim 1, wherein said method comprises imaging a tissue in vivo or in vitro.

9. The method claim 1, wherein said method comprises imaging a plurality of tissues in vivo or in vitro.

10. The method of claim 1, wherein said magnetic resonance imaging is multimodal imaging.

11. The method of claim 10, wherein said multimodal imaging is PET-MM or SPECT-MRI.

12. The method of claim 1, wherein said method further generates one or more of background removal, unambiguous detection of smart agent activation, or targeted agent binding events.

13. The method of claim 1, wherein said maps are generated using a pulse sequence selected from the group consisting of rapid acquisition with refocused echoes (RARE), multi-Spin echo (MSE) pulse sequence, multi-gradient echo (MGE), T1rho mapping, intermolecular multiple quantum coherences, ultrashort echo time relaxometry, and dispersion imaging.

14. The method of claim 13, wherein a combination of two or more of said pulse sequences are utilized.

15. A system for visualizing a contrast agent by magnetic resonance imaging, the system comprising:
   a) at least one contrast agent; and
   b) computer software and a computer processor configured to collect images of said at least one contrast agent, generate $T_1$, $T_2$, and $T_2^*$, and quantitative susceptibility maps, process said maps using a machine learning algorithm trained to recognize said contrast agent to generate processed maps; and generate quantitative maps of said contrast agent concentration, identity, and functional state from said processed maps.

16. The system of claim 15, wherein said processing step further comprises a pre-processing step.

17. The system of claim 15, wherein said machine learning algorithm comprises radial basis function neural network training.

18. The system of claim 15, wherein said at least one contrast agent is at least two contrast agents and each of said agents are represented by different colors on said quantitative maps.

19. The system of claim 15, wherein different states of the same contrast agent are represented by different colors on said quantitative maps.

20. The system of claim 15, wherein said contrast agent is one or more of Gd(III)-daa, Gd(III) biotin, Feridex, MPIO, and super paramagnetic iron oxide SPIO.

* * * * *